United States Patent [19]

Drent

[11] Patent Number: 4,731,202
[45] Date of Patent: Mar. 15, 1988

[54] PROCESS FOR THE HYDROCARBOXYLATION OF ACETYLENICALLY UNSATURATED COMPOUNDS

[75] Inventor: Eit Drent, Amsterdam, Netherlands

[73] Assignee: Shell Oil Company, Houston, Tex.

[21] Appl. No.: 836,777

[22] Filed: Mar. 5, 1986

[30] Foreign Application Priority Data

Mar. 12, 1985 [GB] United Kingdom ............... 8506367

[51] Int. Cl.$^4$ ............................................. C07C 51/14
[52] U.S. Cl. ................................. 260/544 A; 260/546
[58] Field of Search ........................... 260/546, 544 A

[56] References Cited

U.S. PATENT DOCUMENTS 3,641,137  2/1972  Fenton ................................. 260/546
4,414,160  11/1983  Erpenbach et al. ............ 260/544 A Primary Examiner—Donald B. Moyer
Assistant Examiner—L. Hendriksen

[57] ABSTRACT

The hydrocarboxylation of alkynes with CO and a carboxylic acid in the presence of a catalyst prepared by combining a compound of divalent palladium and tri-organic phosphine is carried out by using a ratio of mols phosphine per gramatoms of palladium of more than 15 and, preferably, in the presence of benzenephosphonic acid.

20 Claims, No Drawings

PROCESS FOR THE HYDROCARBOXYLATION OF ACETYLENICALLY UNSATURATED COMPOUNDS

FIELD OF THE INVENTION

The invention relates to a process for the hydrocarboxylation of an acetylenically unsaturated compound by reaction with carbon monoxide and a carboxylic acid in the liquid phase.

BACKGROUND OF THE INVENTION

It is generally known that acetylenically unsaturated compounds can be hydrocarboxylated by reaction with carbon monoxide and a carboxylic acid to yield carboxylic anhydrides.

According to a process known from U.S. Pat. No. 3,641,137 a catalytic system for such reactions is formed by combining a compound of divalent palladium with an organic phosphine, in a quantity of organic phosphine generally in excess (for example 10–300%) of that stoichiometrically required to form a complex with the palladium metal. A ratio mol of organic phosphine to gramatom of divalent palladium of 4 was reported in that patent for the two examples of this known process, corresponding to an excess of 100%. This known process has a very low reaction rate, which renders it unattractive for use on a commercial scale.

Investigations with increased molar ratio of organic phosphine to gramatom of divalent palladium, to a value in excess of 300%, have still shown a low rate of reaction.

SUMMARY OF THE INVENTION

It has now been found that a substantially improved process for the hydrocarboxylation of an acetylenically unsaturated compound by reaction with carbon monoxide and a carboxylic acid results from conducting the reaction in the presence of a catalyst system formed by combining divalent palladium with an organic phosphine in a high molar ratio of the phosphine to the palladium.

The invention, therefore, is a process for the hydrocarboxylation of an acetylenically unsaturated compound which comprises reacting the acetylenically unsaturated compound with carbon monoxide and a carboxylic acid in the liquid phase and in the presence of a catalyst system formed by combining a compound of divalent palladium and a tri-organic phosphine in a ratio of mols of tri-organic phosphine to gramatoms of divalent palladium which is greater than 15.

The process of this invention provides a substantially enhanced rate of reaction as well as high selectivities in the production of the carboxylic anhydrides. The selectivity to carboxylic anhydrides, expressed in a percentage, is defined as $$\text{selectivity} = \frac{a}{b} \times 100$$

wherein "a" is the amount of acetylenically unsaturated compound that has been converted into carboxylic anhydrides and "b" is the total amount of acetylenically unsaturated compound that has been converted.

DESCRIPTION OF THE PREFERRED EMBODIMENTS

This invention centers upon certain aspects of a catalyst system for use in the hydrocarboxylation reaction of an acetylenically unsaturated compound by reaction with carbon monoxide and a carboxylic acid. In general, other aspects of the process may be suitably conducted under conventional practice, for instance as described in the aforementioned U.S. Pat. No. 3,641,137 of D. M. Fenton, the disclosure of which is incorporated herein by this reference.

The process according to the invention may be carried out using as one reactant a wide variety of acetylenically unsaturated compounds, including such compounds which carry one or more substituents which are essentially inert under the hydrocarboxylation reaction conditions, such as halogen atoms and cyano, ester, alkoxy and aryl groups. In addition, suitable acetylenically unsaturated compound may contain one or more substituents which are not inert under the reaction conditions, for example hydroxy groups. The fate of such groups will depend on the precise reaction conditions. One or more acetylenically unsaturated bonds may be present in any position in the carbon chain. Very good results have been obtained with the unsubstituted alkynes, particularly with those having up to 20 carbon atoms per molecule, more particularly with ethyne and propyne. Other examples of suitable alkynes are 1-butyne, 2-butyne, 1-pentyne, 1-hexyne, 1-heptyne, 1-octyne, 2-octyne, 4-octyne, 5-methyl-3-heptyne, 4-propyl-2-pentyne, 1-nonyne, benzylethyne and cyclohexylethyne. Mixtures of two or more acetylenically unsaturated compounds are also very suitable.

A wide range of carboxylic acids may be used as reactant in the process according to the invention. For example, the carboxylic acid may be aliphatic, cycloaliphatic or aromatic, and may carry one or more essentially inert substituents, for example those described hereinbefore for the acetylenically unsaturated compound. The carboxylic acid suitably contains up to 20 carbon atoms. One or more carboxylic groups may be present, in which case different products can be obtained as desired depending upon the molar ratio of reactants used. The carboxylic acid may be, for example, an alkanoic acid or an alkenoic acid. Examples for suitable carboxylic acids are formic acid, acetic acid, propionic acid, n-butyric acid, isobutyric acid, pivalic acid, n-valeric acid, n-caproic acid, caprylic acid, capric acid, decanoic acid, lauric acid, myristic acid, palmitic acid, stearic acid, benzoic acid, o-phthalic acid, m-phthalic acid, terephthalic acid, benzoic acid and toluic acid. Examples of alkenoic acids are acrylic acid, propiolic acid, methacrylic acid, crotonic acid, isocrotonic acid, oleic acid, maleic acid, fumaric acid, citraconic acid and mesaconic acid. Mixtures of carboxylic acids are suitably used.

If an alkanoic acid having n+1 carbon atoms per molecule is reacted with an alkylene having n carbon atoms per molecule, a symmetrical anhydride is produced. Otherwise, a mixed anhydride is initially produced.

If it is desired to prepare a particular acid by the process according to the invention, it may for example be convenient to react one mol of said acid with the corresponding alkyne having one less carbon atom to produce the symmetric anhydride, to hydrolyse this anhydride to produce two mol of acid and to recycle one mol of said acid back to the first stage of the process.

Depending on the presence of further compounds, further reactions may take place. For example, if the process according to the invention is carried out in the presence of an amine, this amine may react with the carboxylic anhydride with formation of a carboxylic acid and an amine carboxylate. For example, reaction of propyne with carbon monoxide and methacrylic acid in the presence of piperidine yields 1-methacryloylpiperidine in high yield.

The relative proportion of the carboxylic acid and the acetylenically unsaturated compound in the process is not a critical aspect of the invention and may vary over a wide range. The molar ratio of carboxylic acid reacted to the acetylenically unsaturated reactant is preferably in the range of from 0.1:1 to 10:1.

The carbon monoxide required for the process may be supplied in substantially pure form, or diluted with an inert gas, for example nitrogen. The presence of more than minor amounts of hydrogen in the gas stream is undesirable since hydrogenation of the acetylenically unsaturated compound then takes place under the reaction conditions. Generally it is preferred that the amount of hydrogen in the gas stream should be less than 5% by volume.

The catalyst system of the process of the invention combines a divalent palladium compound with a tri-organic substituted phosphine. The ratio of mols of tri-organo phosphine to gramatom of divalent palladium is necessarily greater then 15. Preference can be expressed for a ratio of at least about 20, while a ratio of at least about 25 is considered more preferred and a ratio of about 50 is considered most preferred. Higher ratios, e.g., up to 2000 can be used, although it is generally preferred that this ratio of catalyst components be less than 500.

According to a preferred embodiment of the present invention the tri-organic phosphine has the general formula I

in which $R^1$ represents an optionally substituted aryl group and $R^2$ and $R^3$ each represent an optionally substituted alkyl, optionally substituted cycloalkyl or optionally substituted aryl group, or $R^2$ and $R^3$ together represent an optionally substituted alkylene or optionally substituted phosphacyloalkylene group. However, the use of trialkylphosphines or tricycloalkylphosphines is not excluded. Preferably, in the general formula I any alkyl group has up to 20 carbon atoms and any cycloalkyl group up to 7 carbon atoms and any aryl group up to 18 carbon atoms in the ring. Any aryl group may be an anthryl, naphthyl or, more preferably a phenyl group. Phosphines of the general formula I in which $R^1$ and $R^2$ each represent an optionally substituted phenyl group are a preferred group of phosphines; within this group those phosphines in which $R^3$ also represents an optionally substituted phenyl group are particularly preferred. Very good results have been obtained with triphenylphosphine. Other examples of suitable phosphines are phenyldiethylphosphine, ethyldiphenylphosphine, phenyldipropylphosphine and propyldiphenylphosphine.

An optionally substituted alkylene group formed by $R^2$ and $R^3$ suitable has in the range of from 4 to 9, for example from 6 to 8 carbon atoms, and such a group may form a monocyclic or a bicyclic ring containing the phosphorous atom. An example of such a compound is 7-n-eicosylphosphabicyclo[2,2,1]heptane.

Another preferred group of tri-organic phosphines are those of the general formula I in which $R^3$ represents a chain of carbon atoms ending with the group $-PR^4R^5$, in which $R^4$ represents an optionally substituted phenyl group and $R^5$ an optionally substituted alkyl, optionally substituted cycloalkyl or optionally substituted phenyl group. Preferably, $R^4$ and $R^5$ are equal to $R^1$ and $R^2$, respectively. The chain of carbon atoms suitably comprises 2 to 6 carbon atoms. Examples of suitable phosphines are 1,2-di(diphenylphosphino)ethane, 1,2-diphenylphosphino)ethane, 1,2-di(diphenylphosphino)ethyne, 1,2-di(ditrifluoromethylphosphino)ethane, 1,2-di(diphenylphosphino)benzene, 1,2-di(diphenylphosphino)-3,3,4,4-tetrafluoro-1,2-cyclobutene, 1,2-di(diphenylphosphino)-3,3,4,4,5,5-hexafluoro-1,2-cyclopentene, 1,2-di(diphenylphosphino)-3,3,4,4,5,5,6,6-octafluoro-1,2-cyclohexene, bis(o-diphenylphosphinophenyl)phenylphosphine and tris(o-diphenylphosphinophenyl)phenylphosphine.

Mixtures of two or more tri-organic phosphines may be used.

It has also been found in the practice of the invention that even more enhanced reaction rates can be obtained, without reduction of high selectivity to carboxylic anhydrides, when benzenephosphinic acid and/or a 2-mono-, 2,2-di- and/or 2,2,2-trihaloalkanoic acid is also incorporated in the catalytic system. This alkanoic acid is preferably acetic acid. Among the halo atoms chlorine and fluorine atoms are preferred. Very good results have been obtained with trifluoroacetic acid. Benzenephosphonic acid and the 2-mono-, 2,2-di- and 2,2,2-trihaloalkanoic acids are suitably used in combination with triarylphosphines in which the aryl group is unsubstituted or carries an electron-donating substituent. Combination of orthophosphonic acid with triarylphosphines in which the aryl group is unsubstituted or carries an electron-donating substituent does not enhance the reaction rate. Examples of electron-donating substituents are p-alkoxy groups (para with respect to the C—P bond), particularly those having not more than 5 carbon atoms in the alkoxy group, for example p-methoxy and p-ethoxy groups. An example of such a phosphine is tri(p-methoxyphenyl)phosphine. Other examples of suitable electron-donating groups are methyl, ethyl, n-propyl, isopropyl, tert.-butyl, dimethylamino and diethylamino groups.

If desired, a triarylphosphine in which each aryl group carries an electron-withdrawing substituent may be used; such phosphines are suitably used in combination with p-toluenesulphonic acid, orthophosphonic acid and/or a 2-mono-, 2,2-di- and/or 2,2,2-trihaloalkanoic acid. Among the halo atoms chlorine and fluorine atoms are preferred. Very good results have been obtained with trifluoroacetic acid. Examples of electron-withdrawing substituents are chlorine, bromine, monochloromethyl, trichloromethyl, trifluoromethyl, nitro and m-methoxy (meta with respect to the C—P bond) groups. Very good results have been obtained with chlorine atoms, particularly with tri(m-chlorophenyl)phosphine.

The number of equivalents of the tri-organic phosphine which is used per equivalent of benzenephosphonic acid, 2-mono-, 2,2-di- or 2,2,2-trihaloalkanoic acid, p-toluenesulphonic acid or orthophosphoric acid, if used at all, is not critical and may vary between wide limits. Suitably, in the range of from 0.5 to 50 equivalents of the tri-organic phosphine are used per equivalent of such acid.

Both homogeneous and heterogeneous palladium catalyst components may be used in the process according to the invention. Homogeneous palladium compounds are preferred. Suitable homogeneous catalysts are the salts of palladium with, for example, nitric acid, a sulphuric acid or alkanonic acids having not more than 12 carbon atoms per molecule. Salts of hydrohalogenic acids may, in principle, be used, but they have the drawback that the halogen ion may have a corrosive effect. A compound used by preference is palladium acetate. Moreover, palladium complexes may be use, for instance palladium acetylacetonate, tetrakistriphenylphosphinepalladium, bis-tri-o-tolylphosphinepalladium acetate or bistriphenylphosphinepalladium sulphate. Palladium bonded to an ion exchanger, for instance, an ion exchanger comprising sulphonic acid groups, is an example of a suitable heterogenous catalyst.

The quantity of divalent palladium is not critical. Preference is given to the use of quantities in the range between $10^{-5}$ and $10^{-1}$ gramatom palladium per mol of acetylenically unsaturated compound.

A separate solvent is not essential in the process according to the invention, and often an excess of one of the reactants, usually the carboxylic acid, may form a convenient liquid phase. However, it may in some cases be desirable to use a separate solvent, in which case an inert solvent may be used. A suitable solvent may, for example, be selected from sulphoxides and sulphones, for example dimethyl sulphoxide, diethyl sulphoxide, dimethyl sulphone, diethyl sulphone, methyl ethyl sulphone, diisopropyl sulphone, methyl butyl sulphone or tetrahydrothiophene 1,1-dioxide (also referred to as "sulfolane"), 2-methylsulfolane, 3-methylsulfolane, 2-methyl-4-butylsulfolane, aromatic hydrocarbons, for example benzene, toluene or one or more of the xylenes, ketones, for example acetone or methyl isobutyl ketone, esters, for example methyl acetate and butyrolacetone, and N-methylpyrrolidone, and ethers. Very good results have been obtained with ethers, in particular with anisole and diphenyl ether. Other examples of suitable ethers are 2,3,8-trioxanonane (also referred to as "diglyme"), dimethyl ether, diethyl ether, diisopropyl ether, methyl t-butyl ether, tetrahydrofuran, 4-dioxane, 1,3-dioxane and the dioxolanes.

The process according to the invention permits the use of very mild reaction conditions. Temperatures in the range of from 50° C. to 200° C. are generally suitable, while temperatures in the range from, 100° C. to 150° C. are considered preferred. The pressure at which the process is carried out is not critical and may vary over a wide range. Generally, a pressure in the range of from 1 to 100 bar is suitable, with pressures of from 5 to 50 bar being preferred. Pressures higher than 100 bar may be used, but are usually unnecessary and economically unattractive.

The following Examples are intended to further illustrate certain preferred embodiments of the invention without limiting its broader scope.

EXAMPLES 1-10 and Comparative Experiments A-C

In a series of experiments, a 250-ml magnetically stirred Hastelloy C autoclave ("Hastelloy" is a trade mark) was charged with a solvent (40 ml), a carboxylic acid (10 ml) and a catalytic system formed by combining in the autoclave palladium acetate (0.2 mmol), a phosphine and, in some cases, a protonic acid. The specific solvent, carboxylic acid, phosphine and protonic acid used in each of the experiments are identified in the following Table, together with the relative amounts of phosphine and protonic acid. The ratio of mols of phosphine to gramatoms of palladium is 15 in Comparative Experiment A and 50 in Examples 1-10 and Comparative Experiments B and C.

For each experiment the autoclave was flushed with carbon monoxide, filled with propyne at a partial pressure of 2 bar and with carbon monoxide at a partial pressure of 20 bar, sealed and heated to a temperature of 115° C. for the reaction time specified in the Table. Then, the contents of the autoclave were analyzed by means of gas-liquid chromatography. The resulting reaction rates and selectivities to anhydrides are presented in the Table.

Comparison of the results of Example 1 with those of Comparative Experiment A shows that increasing the ratio of mols of phosphine per gramatoms of palladium from 15 to 50 increases the reaction rate by a factor of almost 6.

Examples 1-10 were in accordance with the invention, while Comparative Experiments A-C were not.

Comparison of results of Examples 2 and 3 shows that the presence of benzenephosphonic acid has increased the reaction rate in diphenyl ether by a factor 4, without reducing the high selectivity to methacrylic anhydride.

Comparison of the results of Examples 4 and 5 shows that the presence of benzenephosphonic acid has increased the reaction rate in anisole by a factor 2.6, without changing the high selectivity to methacrylic anhydride.

Comparison of the results of Examples 2 and 6 shows that the presence of trifluoroacetic acid has increased the reaction rate by a factor 1.6 with a slight increase of the selectivity to methacrylic anhydride.

Comparison of the results of Examples 2 and 7 shows that combination of orthophosphoric acid with triphenylphosphine does not enhance the reaction rate.

Examples 8, 9 and 10 show that use of tri(m-chlorophenyl)phosphine in combination with p-toluenesulphonic acid, trifluoroacetic acid or orthophosphoric acid provides good reaction rates and high selectivities to anhydrides.

Comparison of the results of Example 2 with those of Comparative Experiment B shows that the presence of p-toluenesulphonic acid with triphenylphosphine results in an almost complete absence of catalytic activity.

Comparison of the results of Example 2 with those of Comparative Experiment C shows that the presence of hydrogen chloride with triphenylphosphine results in a considerable reduction of catalytic activity.

TABLE

| Example No. | Comparative Experiment | CATALYST | | | | Carboxylic acid | Solvent |
|---|---|---|---|---|---|---|---|
| | | Phosphine | Amount, mmol | Protonic acid | Amount, mmol | | |

TABLE-continued

| Example No. | Comparative Experiment | Phosphine | amount | Acid | amount | Carboxylic acid | Solvent |
|---|---|---|---|---|---|---|---|
| | A | triphenylphosphine | 3 | none | | acetic acid | anisole |
| 1 | | " | 10 | none | | " | " |
| 2 | | " | 10 | none | | methacrylic acid | diphenyl ether |
| 3 | | " | 10 | benzenephosphonic acid | 10 | " | diphenyl ether |
| 4 | | " | 10 | none | | " | anisole |
| 5 | | " | 10 | benzenephosphonic acid | 10 | " | " |
| | B | " | 10 | p-toluenesulphonic acid | 10 | " | diphenyl ether |
| 6 | | " | 10 | trifluoroacetic acid | 5 | " | diphenyl ether |
| 7 | | " | 10 | orthophosphoric acid | 10 | " | diphenyl ether |
| | C | " | 10 | hydrogen chloride | 10 | " | diphenyl ether |
| 8 | | tri(m-chlorophenyl)-phosphine | 10 | p-toluenesulphonic acid | 10 | acetic acid | anisole |
| 9 | | tri(m-chlorophenyl)-phosphine | 10 | trifluoroacetic acid | 10 | methacrylic acid | diphenyl ether |
| 10 | | tri(m-chlorophenyl)-phosphine | 10 | orthophosphoric acid | 10 | " | diphenyl ether |

| Example No. | Comparative Experiment | Reaction time h | Reaction rate, mol propyne per gram atom Pd per h | Selectivity, % to | |
|---|---|---|---|---|---|
| | A | 2 | 60 | total of acetic anhydride, acetic methacrylic anhydride and methacrylic anhydride | 95 |
| 1 | | 2 | 350 | total of acetic anhydride, acetic methacrylic anhydride and methacrylic anhydride | 100 |
| 2 | | 2 | 250 | methacrylic anhydride | 95 |
| 3 | | 0.5 | 1000 | " | 95 |
| 4 | | 2 | 350 | " | 95 |
| 5 | | 1 | 900 | " | 95 |
| | B | 5 | extremely low | not determined | |
| 6 | | 1.3 | 400 | methacrylic anhydride | 96 |
| 7 | | 2 | 250 | " | 95 |
| | C | 5 | 30 | " | 52 |
| 8 | | 2 | 150 | acetic anhydride | 13 |
| | | | | acetic methacrylic anhydride | 68 |
| | | | | methacrylic anhydride | 13 |
| 9 | | 1 | 300 | methacrylic anhydride | 95 |
| 10 | | 1.5 | 400 | " | 95 |

EXAMPLE 11

The experiment of Example 3 was repeated in the presence of piperidine (5 ml). The reaction rate was 500 mol of propyne per gramatom of palladium per hour with a total selectivity to methacrylic anhydride and 1-methacryloylpiperidine of 95%. The piperidine was quantitatively converted into 1-methacryloylpiperidine.

I claim as my invention:

1. In a process for the hydrocarboxylation of acetylenically unsaturated compounds of the formula RC≡CR, wherein each R is individually selected from the group consisting of hydrogen and alkyl groups having from 1 to about 8 carbon atoms, which comprises reacting the acetylenically unsaturated compounds with carbon monoxide and a carboxylic acid in the liquid phase at a temperature in the range from 50° C. to 200° C. and in the presence of a catalyst system formed by combining a divalent palladium compound with a tri-organic phosphine, the improvement which comprises combining the said divalent palladium compound with the said tri-organic phosphine in a ratio of mols of tri-organic phosphine to gramatoms of divalent palladium which is at least about 25.

2. The process of claim 1, wherein the ratio of mols of tri-organic phosphine to gramatoms of divalent palladium is less than 500.

3. The process of claim 2, wherein the tri-organic phosphine has the formula

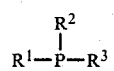

wherein $R^1$ represents an aryl group, and $R^2$ and $R^3$ each represent an alkyl, cycloalkyl or aryl group, or $R^2$ and $R^3$ together represent an alkylene or phosphacyloalkylene group.

4. The process of claim 3, wherein $R^1$, $R^2$ and $R^3$ each individually represents a phenyl group.

5. The process of claim 4, wherein the phosphine is triphenylphosphine.

6. The process of claim 3, wherein the catalyst system also comprises benzenephosphonic acid in an amount of 0.02 to 2.0 equivalents of benzenephosphonic acid per equivalent of phosphine.

7. The process of claim 3, wherein the catalyst system also comprises one or more 2-mono-, 2,2-di- or 2,2,2-trihaloalkanoic acids.

8. The process of claim 7, wherein the haloalkanoic acid is a chloro-or fluoroalkanoic acid.

9. The process of claim 7, wherein the substituted alkanoic acid is a substituted acetic acid.

10. The process of claim 8, wherein the substituted alkanoic acid is a substituted acetic acid.

11. The process of claim 10, wherein the substituted alkanoic acid is trifluoroacetic acid.

12. The process of claim 4, wherein each of the phenyl groups carries an electro-withdrawing substituent and the catalyst system incorporates orthophosphoric acid.

13. The process of claim 12, wherein the electron-withdrawing substituent is a chlorine atom.

14. The process of claim 13, wherein the phosphine is tri(m-chlorophenyl)phosphine.

15. The process of claim 1, wherein the divalent palladium compound is palladium acetate.

16. The process of claim 1, wherein the liquid reaction phase contains an ether solvent.

17. The process of claim 1, wherein the reaction is carried out at a total pressure in the range from 1 to 100 bar.

18. The process of claim 1, wherein the acetylenically unsaturated compound is an alkyne.

19. In a process for the hydrocarboxylation of an alkyne to produce a carboxylic anhydride, which comprises reacting an alkyne having up to 20 carbon atoms with carbon monoxide and a carboxylic acid in the liquid phase at a temperature in the range from 50° C. to 200° C. and at a pressure in the range from 1 to 100 bar and in the presence of a catalyst system formed by combining a divalent palladium compound with a tri-organic phosphine of the formula

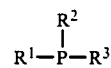

wherein $R^1$ represents an aryl group, and $R^2$ and $R^3$ each represent an alkyl, cycloalkyl or aryl group, or $R^2$ and $R^3$ together represent an alkylene or phosphacycloalkylene group, the improvement which comprises combining the said divalent palladium compound with the said tri-organic phosphine in a ratio of mols of tri-organic phosphine to gramatoms of divalent palladium which is between about 25 and 500.

20. The process of claim 19, wherein the catalyst system also comprises benzenephosphonic acid in an amount of 0.02 to 2.0 equivalents of benzenephosphonic acid per equivalent of phosphine.

* * * * *